United States Patent [19]

Mitsutake et al.

[11] Patent Number: 5,017,364

[45] Date of Patent: May 21, 1991

[54] PASTE-LIKE DENTIFRICE COMPOSITION

[75] Inventors: Hiromi Mitsutake, Yokohama; Hideomi Saitoh, Sagamihara; Koichiro Nagata, Yokkaichi, all of Japan

[73] Assignee: Ajinomoto Co., Inc., Tokyo, Japan

[21] Appl. No.: 422,460

[22] Filed: Oct. 17, 1989

[30] Foreign Application Priority Data

Oct. 20, 1988 [JP] Japan ................. 63-264464

[51] Int. Cl.$^5$ ................. A61K 7/16; A61K 7/22
[52] U.S. Cl. ................. 424/54; 424/49
[58] Field of Search ................. 424/49, 54

[56] References Cited

U.S. PATENT DOCUMENTS

| | | | |
|---|---|---|---|
| 2,689,170 | 9/1954 | King | 424/54 |
| 2,772,203 | 11/1956 | Salzmann | 424/54 |
| 2,772,204 | 11/1956 | King | 424/54 |
| 2,909,535 | 10/1959 | Jungermann | 424/54 |
| 4,160,822 | 7/1979 | Hashimoto et al. II | 424/52 |
| 4,335,102 | 6/1982 | Nakashima et al. | 424/52 |
| 4,618,488 | 10/1986 | Maeyama et al. | 424/49 |
| 4,865,839 | 9/1989 | Saso II | 424/49 |

OTHER PUBLICATIONS

Hashimoto et al. I C.A. 90:174531x (1979).
L10N C.A. 95:1922263 (1981).
SASO I C.A. 109:155987v (1988).

*Primary Examiner*—Shep K. Rose
*Attorney, Agent, or Firm*—Oblon, Spivak, McClelland, Maier & Neustadt

[57] ABSTRACT

Herein is disclosed a paste-like dentifrice composition containing, as the foaming agent, from 0.1 to 5.0% by weight of highly pure N-long-chain acylglutamate which contains not more than 1.0% by weight of higher fatty acid(s), either in the free form or in the salt form.

3 Claims, No Drawings

PASTE-LIKE DENTIFRICE COMPOSITION

BACKGROUND OF THE INVENTION

1. Field of the Invention

The present invention relates to a paste-like dentifrice composition. More specifically, the present invention relates to such a composition containing, as its foaming agent, N-long-chain acylglutamate which assures an increased level of safety, in such a manner that the use of this substance does not involve problems such as a change in taste of foods after tooth-brushing.

2. Discussion of the Background

A dentifrice contains as one of its components a foaming agent which provides such actions as a cleaning action, a dispersing and emulsifying action, and a foaming action. A surface active agent is used for this purpose.

A surface active agent used as a foaming agent in a dentifrice composition reduces the surface tension of the composition when used, thereby promoting the cleaning effect of the dentifrice composition, and promotes the dispersion and permeation of various medically effective agents contained in the composition, thereby enhancing their effects. The surface active agent also forms foam when the dentifrice is used, thereby providing the user with a sense of assurance. A surface active agent thus can be said to be an essential component of a dentifrice composition.

A surface active agent to be used as one of the components of a dentifrice composition, therefore, must be able to exhibit excellent performance in, e.g., reducing the surface tension and foaming. In addition, because a dentifrice composition is used in the mouth, the surface active agent contained therein must have satisfactory properties in terms of taste, odor, etc. Hitherto, anionic surface active agents, such as sodium alkylsulfate, sodium acylsarcosinate, α-olefin sulfonate, and coconut nomoglyceride sodium sulfate, have been used. In particular, sodium alkylsulfate, which is excellent in terms of its performance and taste, is used most commonly. However, the use of this substance as the surface active agent of a dentifrice composition involves a great drawback: after the use of the dentifrice composition, possibly because of the adhesion of the substance in the mouth, e.g., on the taste buds of the tongue or the mucous membrane of the mouth, the taste of food taken in the mouth after tooth-brushing changes. Another problem is that, sodium alkylsulfate when contained in a dentifrice composition slightly stimulate the mucous membrane of the mouth and deactivates the enzyme which has been incorporated as a medically effective agent.

Recently, the level of safety of such surface active agents has been questioned, and various studies have been conducted to enable a safer surface active agent to be used as the foaming agent in a dentifrice composition. A proposal has been made, for example, to use N-long-chain acylglutamate in a dentifrice composition (Japanese Patent Publication (Kokai) No. SHO 45-24480 (1970)). It is said that N-long-chain acylglutamate, which has no toxicity and only very mildly stimulates the skin or the mucous membrane, while possessing excellent cleaning, foaming, and emulsifying action, and is excellent in resistance to hard water, is a very effective foaming agent for a dentifrice composition because of various advantageous properties such as those mentioned above.

With respect to the influence of N-long-chain acylglutamate on the taste of dentifrice compositions, it is reported that, if a dentifrice composition contains a large amount of N-long-chain acylglutamate having a relatively lower acyl group (e.g., coconut oil fatty acid acyl), the composition has a strongly bitter taste (Japanese Patent Publication (Kokai) No. SHO 58-45402 (1983)). Hitherto, however, nothing about the influence of impurities in N-long-chain acylglutamate has been known.

SUMMARY OF THE INVENTION

Accordingly, an object of the present invention is to improve the taste of a dentifrice composition containing N-long-chain acylglutamate.

The present invention thus provides a paste-like dentifrice composition which satisfies the above object of the invention and other objects which will become apparent from the description of the invention given hereinbelow.

In an aspect of the present invention, there is provided a paste-like dentifrice composition containing, as the foaming agent, from 0.1 to 5.0% by weight of highly pure N-long-chain acylglutamate which contains, as contaminants, not more than 1.0% by weight of higher fatty acid(s) either in the free form or in the salt form.

DETAILED DESCRIPTION OF THE INVENTION

The present inventors have conducted studies in detail on the influence of N-long-chain acylglutamate on the taste of a paste-like dentifrice composition when the substance is incorporated into such a composition. As a result, it has been found that, if highly pure N-long-chain acylglutamate which contains, as impurities, not more than 1.0% by weight, preferably not more than 0.5% by weight, of higher fatty acid(s) (in the free state and/or in the salt form) is used in a dentifrice composition, it is possible to avoid a "dusty" taste of the dentifrice composition, as well as the phenomenon known as "the juice effect", in which phenomenon when, after toothbrushing with the use of a dentifrice composition, the user ingests a strongly sour food, typically orange juice, the food tastes much different. See Japanese Patent Publication (Kokai) No. SHO 47-43830 (1972). The present invention has been accomplished on the basis of the above-described knowledge.

The gist of the present invention therefore resides in a paste-like dentifrice composition containing, as the foaming agent, from 0.1 to 5.0% by weight, preferably from 0.3 to 3.0% by weight, of N-long-chain acylglutamate which contains not more than 1.0% by weight of higher fatty acid(s), either in the free state or in the salt form.

If the content of N-long-chain acylglutamate is less than 0.1% by weight, the foaming ability of the dentifrice composition deteriorates. On the other hand, if that content exceeds 5.0% by weight, the composition fails to exhibit an adequate softness which is required of a paste-like dentifrice composition.

Methods which may be used to obtain highly pure N-long-chain acylglutamate include the following. In a first method, glutamic acid is caused to react with a higher fatty acid chloride in the presence of an alkali. In the reaction, glutamic acid is used in an amount of from 1.1 to 1.3 mols per 1 mol of the higher fatty acid chloride, so as to restrain the decomposition of the higher fatty acid chloride. In a second method, impure N-long-chain acylglutamic acid containing several % by weight of higher fatty acid(s) is dried. Thereafter, the higher fatty acid(s) are extracted from the impure N-long-chain acylglutamic acid using a hydrophobic organic solvent such as n-hexane, petroleum ether, petroleum benzine, or toluene, so as to refine the impure N-long-chain acyl glutamic acid.

Although glutamic acid may be L-isomer, D-isomer, or a mixture thereof mixed in any proportion, L-glutamic acid is preferred from the viewpoint of its compatibility with the living body.

The thus obtained highly pure N-long-chain acylglutamic acid is incorporated into a paste-like dentifrice composition as its alkali metal salt such as sodium salt or potassium salt, or its basic amino acid salt such as its addition salt with lysine. When highly pure N-long-chain acylglutamic acid is contained in a dentifrice composition in this way, the properties that it originally possesses, such as its foaming ability and safety, are not spoiled.

Examples of N-long-chain acylglutamates which may be used according to the invention are water-soluble salts of glutamic acid N-substituted by a saturated or an unsaturated acyl group having a carbon number of 8 to 20. Examples of acyl groups which may be used include caprinoyl, lauroyl, tridecanoyl, 2-methyllauroyl, myristoyl, pentadecanoyl, palmitoyl, stearoyl, isostearoyl, and oleoyl. A usable acyl group may alternatively be a coconut oil fatty acid residue, a palm oil fatty acid residue, a hardened beef tallow fatty acid residue, or a mixture of fatty acid residues of coconut oil and hardened beef tallow.

Higher fatty acids which, in the present invention, should be removed from N-long-chain acylglutamic acid are higher fatty acids that remain unreacted during the acylation reaction, and may not only be in their free state but also in their salt form.

A dentifrice composition in general contains, in addition to a foaming agent, other agents, such as those listed below, which are contained when suitable so that they may act as effective components of the composition: an abrasive such as calcium secondary phosphate or its dihydrate, calcium carbonate, calcium pyrophosphate, insoluble sodium metaphosphate, silicic acid anhydride, silicic acid hydrate, alumino-silicate, alumina, or aluminum hydroxide; a viscosity agent such as glycerin, sorbitol, propylene glycol, or polyethylene glycol; a caking agent such as carboxymethyl cellulose, carrageenan, sodium alginate, bee gum, hydroxethyl cellulose, or polyvinyl alcohol; a sweetener such as saccharin sodium, glylcylrrhizin salts, stevioside, neohesperidin dihydrcchalcone, paramethoxy-cinnamic aldehyde, perillartine, or aspartame; and a perfume such as menthol, carvone, or anethole. The composition may further contain a germicide such as a fluoride, e.g., sodium monofluorophosphate, tin fluoride, sodium fluoride, or a chlorohexadiyne salt; a phosphate builder such as sodium phosphate; an enzyme such as dextranase, or amylase; an anti-inflammatory agent such as ε-aminocaproic acid, tranexamic acid, or allantoinate; and a gingival astringent such as sodium chloride.

In order to prepare a paste-like dentifrice composition of the present invention, its components selected from among the above-listed substances are mixed with a suitable amount of water, and the mixture is kneaded. The proportion in which the agents or components of the paste-like dentifrice composition of the present invention, such as a foaming agent, an abrasive, a viscosity agent, a caking agent, a sweetener, a germicide, a builder, an anti-inflammatory agent, and a gingival astringent, are mixed together is not particularly specified, and they may be mixed in a proportion similar to those in a conventionally known paste-like dentifrice composition.

According to the present invention, because the paste-like dentifrice composition contains, as the foaming agent, from 0.1 to 5.0% by weight of N-long-chain acylglutamate containing not more than 1.0% of higher fatty acid, the taste of the composition is improved. However, since the same taste of flavor may be perceived with greatly varying degrees between individuals, various seasoning additives may be added to a base consisting of the paste-like dentifrice composition of the present invention so as to adjust the taste of the composition. Examples which may be used as seasoning additives include a sweetener and/or a perfume, such as those mentioned above. In particular, it is effective to add aspartame, which is weakly acidic and stable to a weakly acidic dentifrice composition in order to sweeten such a composition.

With respect to the foaming agent, in addition to and together with N-long-chain acylglutamate used in accordance with the present invention, a commonly used surface active agent such as sodium lauryl sulfate or sodium lauroyl sarcosinate may be used, without causing any problems.

Hereinafter, the present invention will be described with respect to examples thereof, to specifically illustrate the characteristics of the present invention.

EXAMPLE 1

A paste-like dentifrice composition was prepared employing a normal method. Its components are listed in Table 1 in the proportion shown in the same.

TABLE 1

| COMPONENTS | PROPORTION (% by weight) |
| --- | --- |
| Calcium carbonate | 40.0 |
| Carboxymethyl cellulose | 2.0 |
| Glycerin | 20.0 |
| Saccharin sodium | 0.1 |
| Germicide | 0.1 |
| Sodium N-lauroyl-L-glutamate (wherein no lauric acid was detected) | 2.0 |
| Water | 35.8 |

In order to enable comparison, additional paste-like dentifrice compositions were prepared. The comparison compositions contained the same components in the same proportion as in Example 1 except that they were prepared using therein N lauroyl-L-glutamate (sodium salt) containing various different amounts of lauric acid, as shown in the left column of Table 2.

The thus prepared compositions were tested on their taste when they were used for tooth-brushing by a panel of experts consisting of ten members. The results of the test are shown in Table 2.

In table 2, the mark 3 indicates that a dusty taste was perceived; 2, that a slightly dusty taste was perceived; and 1, that no dusty taste was perceived.

TABLE 2

| CONTENT OF LAURIC ACID IN N-LAUROYL-L-GLUTAMATE (% by weight) | MARK (AVERAGE POINT) |
| --- | --- |
| 3.5 | 3 |
| 2.1 | 3 |
| 1.0 | 1.5 |
| 0.5 | 1.1 |
| 0.01 | 1.0 |

As is clearly understood from Table 2, the dentifrice composition of the present invention which N-lauroyl-L-glutamate containing not more than 1.0% by weight of lauric acid gives substantially no uncomfortable taste.

EXAMPLE 2 TO 6

Paste like dentifrice compositions (Examples 2 to 6 were prepared, which contained the components listed in Table 3 in the proportion shown the same. These compositions were prepared using therein different types of N-long-chain acyl-L-gluatamate which contained different amounts of higher fatty acids, as shown in Table 4. The thus prepared compositions were subjected to taste tests, described below.

TABLE 3

| COMPONENTS | PROPORTION (% by weight) |
| --- | --- |
| Calcium secondary phosphatedihydrate | 45.0 |
| Carboxymethyl cellulose | 1.0 |
| Glycerin | 10.0 |
| Sorbitol | 10.0 |
| Saccharin sodium | 0.1 |
| Germicide | 0.1 |
| N-lauroyl-L-glutamate | 1.0 |
| Water | 32.8 |

TABLE 4

| EXAMPLE No. | TYPE OF N-LONG-CHAIN ACYL-L-GLUTAMATE | FATTY ACID CONTENT (% by weight) | MARK (AVERAGE POINT) |
| --- | --- | --- | --- |
| 2 | Sodium N-coconut oil fatty acid acyl-L-glutamate | 0.15<br>2.3 | 1.3<br>5.0 |
| 3 | Sodium N-lauroyl-L-glutamate | 0.23<br>3.1 | 1.0<br>5.0 |
| 4 | Sodium N-myristoyl-L-glutamate | 0.15<br>3.0 | 1.1<br>5.0 |
| 5 | Sodium N-stearoyl-L-glutamate | 0.20<br>2.8 | 1.2<br>5.0 |
| 6 | Disodium N-stearoyl-L-glutamate | 0.18<br>3.2 | 1.0<br>5.0 |

In the taste tests, the taste of orange juice ingested after tooth-brushing was tested by the same panel of experts as in Example 1. The results of the tests are also shown in Table 4.

In Table 4, the mark 5 indicates a great change in taste; 4, a considerable change in taste; 3, a slight change in taste; 2, substantially no change in taste; and 1, no change in taste.

As is clearly understood from Table 4, the dentifrice composition of the present invention which contains N-long-chain acyl-L-glutamate containing not more than 1.0% by weight of fatty acid causes substantially no change in the taste of orange juice ingested after the use of the composition of the present invention.

EXAMPLE 7

A weakly acidic (pH 6.8) paste-like dentifrice composition was prepared, which contained the components listed in Table 5 in the proportion shown in the same. This composition contained highly pure N-lauroyl-L-glutamate containing 0.2% by weight of lauric acid, and aspartame was used as the sweetener in the composition. The thus prepared composition was subjected to taste tests, described below.

TABLE 5

| COMPONENTS | PROPORTION (% by weight) |
| --- | --- |
| Calcium secondary phosphate dihydrate | 40.0 |
| Carboxymethyl cellulose | 1.0 |
| Glycerin | 10.0 |
| Sorbitol | 10.0 |
| Aspartame | 0.1 |
| Germicide | 0.1 |
| Sodium N-lauroyl-L-glutamate | 0.5 |
| Water | 38.3 |

In the taste tests, the taste of the composition during tooth-brushing and the taste of orange juice ingested after the tooth-brushing were tested by the same panel of experts as in Example 1.

As a result, neither dusty taste in the composition nor change in the taste of orange juice was perceived.

EXAMPLE 8

A paste-like dentifrice composition was prepared, which contained the components listed in Table 6 in the proportion shown in the same. This composition contained highly pure N-lauroyl-L-glutamate containing 0.2% by weight of lauric acid, and sodium chloride was used in the composition. The thus prepared composition was subjected to taste tests, described below.

TABLE 6

| COMPONENTS | PROPORTION (% by weight) |
| --- | --- |
| Calcium carbonate | 35.0 |
| Carboxymethyl cellulose | 1.0 |
| Glycerin | 10.0 |
| Sorbitol | 10.0 |
| Sodium chloride | 10.0 |
| Germicide | 0.1 |
| Sodium N-lauroyl-L-glutamate | 0.2 |
| Sodium lauryl sulfate | 0.3 |
| Water | 33.4 |

In the taste tests, the taste of the composition during tooth-brushing and the taste of orange juice ingested after the tooth-brushing were tested by the same panel of experts as in Example 1.

As a result, neither dusty taste in the composition nor change in the taste of orange juice was perceived.

EXAMPLE 9

A paste-like dentifrice composition was prepared, which contained the components listed in Table 7 in the proportion shown in the same. This composition contained highly pure N-lauroyl-L-glutamate containing 0.2% by weight of lauric acid, and sodium chloride was used in the composition. The thus prepared composition was subjected to taste tests, described below.

TABLE 7

| COMPONENTS | PROPORTION (% by weight) |
| --- | --- |
| Calcium carbonate | 40.0 |
| Carboxymethyl cellulose | 1.0 |
| Glycerin | 10.0 |
| Sorbitol | 10.0 |
| Sodium chloride | 10.0 |
| Germicide | 0.1 |
| Sodium N-lauroyl-L-glutamate | 0.5 |
| Water | 28.4 |

In the taste tests, the taste of the composition during tooth-brushing and the taste of orange juice ingested after the tooth-brushing were tested by the same panel of experts as in Example 1.

As a result, neither dusty taste in the composition nor change in the taste of orange juice was perceived.

It would be understood from the foregoing description of the present invention, particularly from Examples, that the present invention provides a plate-like dentifrice composition that has an excellent taste free from any "dusty" taste and that is capable of exhibiting improvement in the "juice effect" after the use thereof, while allowing various taste adjusting components to be added thereto in accordance with personal preference.

What is claimed is:

1. A paste-like dentifrice composition containing, as its essential foaming agent, from 0.1 to 0.5% by weight of N-long-chain acylglutamate itself containing not more than 1.0% by weight of impurities that remain unreacted during the acylation reaction, including higher fatty acid(s) either in free form or in salt form, as contaminants, said composition not imparting the well-known change in the taste of orange juice ingested after tooth brushing, known as the orange juice aftertaste phenomenon.

2. A paste-like dentifrice composition according to claim 1, wherein said N-long-chain acylglutamate is N-long-chain acyl-L-glutamate.

3. In a method of employing a dentifrice paste composition which contains as its essential foaming agent from 0.1 to 0.5% by weight of N-long-chain acylglutamate the improvement comprising limiting in said N-long-chain acylglutamate in said paste the content of impurities that remain unreacted during the acylation reaction, including higher fatty acids either in free form or in salt form as contaminant, therein to not more than 0.1% by weight, and toothbrushing with said composition, followed by ingesting orange juice, without imparting the well-known change in the taste of orange juice ingested after tooth brushing, known as the orange juice aftertaste phenomenon.

* * * * *

UNITED STATES PATENT AND TRADEMARK OFFICE
CERTIFICATE OF CORRECTION

PATENT NO. : 5,017,364
DATED : MAY 21, 1991
INVENTOR(S) : HIROMI MITSUTAKE ET AL

It is certified that error appears in the above-identified patent and that said Letters Patent is hereby corrected as shown below:

COLUMN 8;

Claim 1, line 2, "0.5%" should read --5.0%--.

Claim 3, line 3, "0.5%" should read --5.0%--.

Claim 3, line 9, "0.1%" should read --1.0%--.

Signed and Sealed this

Twelfth Day of January, 1993

*Attest:*

DOUGLAS B. COMER

*Attesting Officer*    Acting Commissioner of Patents and Trademarks